US012808003B2

(12) United States Patent
Dai et al.

(10) Patent No.: US 12,808,003 B2
(45) Date of Patent: Nov. 24, 2026

(54) COMPOSITION, KIT AND METHOD FOR DETECTING AND TYPING VIRUSES CAUSING RESPIRATORY TRACT INFECTION AND APPLICATION OF COMPOSITION, KIT AND METHOD

(71) Applicant: SANSURE BIOTECH INC., Changsha (CN)

(72) Inventors: Lizhong Dai, Changsha (CN); Deyong Tan, Changsha (CN); Zhongping Deng, Changsha (CN); Jia Liu, Changsha (CN); Qingzhi Sun, Changsha (CN); Xing Cheng, Changsha (CN); Xiaomei Ren, Changsha (CN); Xiaoliang Chen, Changsha (CN); Junjie Mao, Changsha (CN)

(73) Assignee: Sansure Biotech Inc., Changsha (CN)

( * ) Notice: Subject to any disclaimer, the term of this patent is extended or adjusted under 35 U.S.C. 154(b) by 993 days.

(21) Appl. No.: 17/933,162

(22) Filed: Sep. 19, 2022

(65) Prior Publication Data

US 2023/0183824 A1 Jun. 15, 2023

Related U.S. Application Data

(63) Continuation of application No. PCT/CN2020/096940, filed on Jun. 19, 2020.

(30) Foreign Application Priority Data

Mar. 23, 2020 (CN) ......................... 202010205841.1

(51) Int. Cl.
*C12Q 1/6883* (2018.01)
*C12Q 1/70* (2006.01)

(52) U.S. Cl.
CPC ........... *C12Q 1/701* (2013.01); *C12Q 1/6883* (2013.01)

(58) Field of Classification Search
CPC ............................. C12Q 1/701; C12Q 1/6883; C12Q 2600/166; C12Q 1/6851; C12Q 2531/113; C12Q 2521/107; C12Q 2545/101; C12Q 2563/107
See application file for complete search history.

(56) References Cited

U.S. PATENT DOCUMENTS 6,399,364 B1 * 6/2002 Reeve .................. C12Q 1/6874 435/287.1
8,163,474 B2 * 4/2012 Lu .................... G01N 33/56983 435/7.1

FOREIGN PATENT DOCUMENTS

CN 1548054 A 11/2004
CN 102181579 A 9/2011
CN 104342503 A 2/2015
CN 110172529 A 8/2019
CN 110343784 A 10/2019
CN 111074011 A 4/2020
CN 111074011 B * 7/2020 ............. C12Q 1/701
KR 20200056831 A * 5/2020 ............. C12Q 1/686
WO WO-2021263101 A1 * 12/2021 ............. C12Q 1/686

OTHER PUBLICATIONS

NEB catalog (1998/1999, pp. 121, 284).*
Rothstein et al. (1994) PNAS USA 91: 4155-4159.*
Hodgson (1987, vol. 15, p. 6295).*
Translation of CN111074011B, pp. 1-4, printed Nov. 6, 2025.*
Tianlong Technology, Title of the article: Tianlong Technology Launches Four Nucleic Acid Test Solutions to Facilitate Differential Diagnosis of New Coronavirus, www.bio-equip.com, Feb. 27, 2020.
Victor M Corman, et al., Title of the article: Detection of 2019 novel coronavirus (2019-nCoV) by real-time RT-PCR, vol. 25, 1-8, Euro Surveill, Jan. 23, 2020.
Chen Wei, et al., Title of the article: Comparison of throat swab and sputum specimens for viral nucleic acid detection in four cases of 2019-nCoV infection, vol. 5, 354-358, Chinese Journal of Zoonoses, Feb. 12, 2020.
Guo Yuanyuan, et al, Title of the article: Comparison and analysis of the detection performance of six new coronavirus nucleic acid detection reagents, vol. 49, pp. 2435-2439, Chongqing Medicine, Feb. 12, 2020.
Shirato, Kaya et al., Title of the article: Development of Genetic Diagnostic Methods for Novel Coronavirus, Japanese Journal of Infections Diseases, Feb. 18, 2020.
Wang Xudong et al., Title of the item: Research Status and Application Discussion of 2019 novel coronavirus Nucleic Acid Detection, vol. 38, pp. 81-84, Chinese Journal of Clinical Laboratory Science, Feb. 29, 2020.
Kuang Huihui et al., Title of the article: Detection of nucleic acid of 2019-nCoV in medical laboratory and its practice, vol. 30, pp. 830-833, Chinese Journal of Nosocomiology, Feb. 23, 2020.
Supplementary European Search Report, Application No. EP20927649, Dec. 16, 2022.
International Search Report, International application No., PCT /CN2020/096940, Jan. 4, 2021.
Written Opinion of the International Searching Authority, International application No. PCT /CN2020/096940, Jan. 4, 2021.
The State Intellectual Property Office of People's Republic of China, First Office Action, Application No. 202010205841.1.

* cited by examiner

*Primary Examiner* — Sarae L Bausch
(74) *Attorney, Agent, or Firm* — Flener IP & Business Law

(57) ABSTRACT

Provided is a composition for detecting a novel coronavirus, influenza A virus and influenza B virus; moreover, also provided are a kit including the composition, an application of the kit, and a method for detecting and typing viruses causing respiratory tract infection.

20 Claims, 8 Drawing Sheets

Specification includes a Sequence Listing.

COMPOSITION, KIT AND METHOD FOR DETECTING AND TYPING VIRUSES CAUSING RESPIRATORY TRACT INFECTION AND APPLICATION OF COMPOSITION, KIT AND METHOD

CROSS-REFERENCE TO RELATED APPLICATIONS

This application is a continuation of International Application No. PCT/CN2020/096940, filed on Jun. 19, 2020, which claims priority to Chinese Patent Application No. 202010205841.1, filed on Mar. 23, 2020. The disclosures of the aforementioned applications are hereby incorporated by reference in their entireties.

TECHNICAL FIELD

The present application pertains to the field of molecular biological detection, specifically, to the field of detection of viruses that cause respiratory tract infections. More specifically, the present application is capable of simultaneous detection and typing of novel coronavirus 2019-nCOV, influenza A virus, and influenza B virus.

BACKGROUND

Respiratory diseases caused by respiratory tract infections are common diseases, and the causative pathogens mainly include viruses, bacteria, mycoplasmas, chlamydiae, etc. Among them, common viral pathogens include influenza A viruses and influenza B viruses, which are also the main pathogens of seasonal influenza; and another type of virus that causes respiratory tract infections is coronaviruses.

The envelope of influenza viruses has two very important glycoproteins: hemagglutinin (HA) and neuraminidase (NA). Generally, there are 500 hemagglutinin spikes and 100 neuraminidase spikes distributed on the surface of the influenza viruses, which serve as the basis for influenza A virus typing according to the antigenicity of HA and NA in the influenza viruses. Influenza A viruses can infect humans, mammals, and birds. H1N1, H2N2, and H3N2 subtypes mainly infect humans, and other subtypes mainly infect birds, pigs, horses, and aquatic mammals. There are 12 subtypes of avian influenza viruses that can infect humans, including H5N1, H7N1, H7N2, H7N4, H7N9, H9N2, H10N8, etc. Influenza B viruses are mainly prevalent in the population, and has no subtype classification. The three branches are the Li line, the Yamagata line, and the Victoria line, and their epidemic scales are smaller than that of influenza A viruses. The genetic material of influenza viruses is a negative-sense single-stranded RNA (ss-RNA), which binds to a nucleoprotein and winds into a ribonucleoprotein complex present in a form with an extremely high density. In addition to the ribonucleoprotein complex, there is also an RNA polymerase responsible for RNA transcription. The RNA of influenza viruses is mainly composed of eight segments. The first, second, and third segments encode an RNA polymerase, the fourth segment encodes a hemagglutinin; the fifth segment encodes a nucleoprotein; the sixth segment encodes a neuraminidase; the seventh segment encodes a matrix protein; and the eighth segment encodes a nonstructural protein that can function to splice an RNA.

So far, there are seven kinds of coronaviruses infecting humans, among which coronavirus 229E, coronavirus NL63, coronavirus OC43, and coronavirus HKU1 are common ones, which cause mild conditions after infecting the human respiratory tract and usually do not induce severe illnesses. However, novel coronavirus 2019-nCOV, coronavirus MERSr-COV, and coronavirus SARSr-COV infections will cause very serious infection symptoms in patients, and are highly likely to develop into severe illnesses.

The novel coronavirus is a new type of coronavirus belonging to the genus β, which is named "novel coronavirus (2019-nCOV)" by the World Health Organization. 2019-nCOV has an envelope, and the particles are round or oval, often pleomorphic, with a diameter of 60-140 nm. The genetic characteristics thereof are significantly different from those of SARSr-COV and MERSr-COV. According to the latest research results of researchers, 2019-nCOV is very similar to RaTG13, a bat coronavirus strain previously isolated from Chinese horseshoe bats, with an overall genome similarity of 96.2%. In addition, studies have shown that 2019-nCOV is 85% or more homologous to bat SARS-like coronaviruses (bat-SL-CoVZC45 and bat-SL-CoVZXC21).

The pathogens of respiratory tract infections are extremely diverse. One clinical manifestation may be caused by multiple pathogens, and one pathogen may also cause multiple clinical manifestations, which bring great difficulties to early clinical diagnosis.

For most viruses that cause respiratory tract infections, early treatment will produce better therapeutic effects. For example, once a patient with influenza shows symptoms, he/she should start taking oseltamivir as soon as possible, ideally within 48 hours of symptom onset; when being used for prevention, oseltamivir should also be taken within 48 hours of exposure to a patient with flu. Early diagnosis and early treatment are keys to improving the cure rate and reducing the fatality rate of influenza patients.

For the novel coronavirus, in addition to early detection and early treatment, it is also necessary to control the source of infection in time, so as to stop virus pandemics and outbreaks.

Therefore, distinguishing whether a respiratory tract infection is caused by a novel coronavirus or caused by an influenza A or B virus so as to provide guidance for subsequent prevention and control, treatment, and adoption of targeted measures is the top priority of respiratory disease prevention and control.

Therefore, there is a need in the art for a related product capable of detecting and distinguishing a novel coronavirus, an influenza A virus, and an influenza B virus.

SUMMARY

In view of this, provided in the present application is a composition capable of detecting and typing viruses that cause a respiratory tract infection. The composition includes:

- a novel coronavirus 2019-nCOV forward primer as shown in SEQ ID NO: 1, a novel coronavirus 2019-nCOV reverse primer as shown in SEQ ID NO: 2, and a novel coronavirus 2019-nCOV probe as shown in SEQ ID NO: 3; and at least one of the following two groups:
- a first group: an influenza A virus forward primer as shown in SEQ ID NO: 7, an influenza A virus reverse primer as shown in SEQ ID NO: 8, and an influenza A virus probe as shown in SEQ ID NO: 9; and
- a second group: an influenza B virus forward primer as shown in SEQ ID NO: 10, an influenza B virus reverse primer as shown in SEQ ID NO: 11, and an influenza B virus probe as shown in SEQ ID NO: 12, where fluorescent reporter groups of three probes are different from each other and do not interfere with each other.

Herein, the description "different from each other and do not interfere with each other" means that the fluorescent groups used by the respective probes in the composition are different, and will not affect the detection of each other, i.e., different channels may be used for detection. For example, FAM®, HEX®, ROX®, and CY5® may be used. The absorbance values of these fluorescent groups are not close, and different detection channels may be selected, and therefore, the fluorescent groups will not interfere with each other.

In one embodiment, the composition further includes: a novel coronavirus 2019-nCOV forward primer as shown in SEQ ID NO: 4, a novel coronavirus 2019-nCOV reverse primer as shown in SEQ ID NO: 5, and a novel coronavirus 2019-nCOV probe as shown in SEQ ID NO: 6.

By including the additional SEQ ID NOs: 4-6, the composition of the present invention may further increase the accuracy of novel coronavirus detection, and avoid false negatives such as misses to the greatest extent.

In one specific embodiment, the composition includes: the novel coronavirus 2019-nCOV forward primer as shown in SEQ ID NO: 1, the novel coronavirus 2019-nCOV reverse primer as shown in SEQ ID NO: 2, and the novel coronavirus 2019-nCOV probe as shown in SEQ ID NO: 3; and the influenza A virus forward primer as shown in SEQ ID NO: 7, the influenza A virus reverse primer as shown in SEQ ID NO: 8, and the influenza A virus probe as shown in SEQ ID NO: 9.

The above embodiment may be used when there is no actual clinical need to detect an influenza B virus, and a simultaneous detection of a novel coronavirus and an influenza A virus is needed, thereby reducing costs.

In one specific embodiment, the composition includes the novel coronavirus 2019-nCOV forward primer as shown in SEQ ID NO: 1, the novel coronavirus 2019-nCOV reverse primer as shown in SEQ ID NO: 2, and the novel coronavirus 2019-nCOV probe as shown in SEQ ID NO: 3; and the influenza B virus forward primer as shown in SEQ ID NO: 10, the influenza B virus reverse primer as shown in SEQ ID NO: 11, and the influenza B virus probe as shown in SEQ ID NO: 12.

The above embodiment may be used when there is no actual clinical need to detect the influenza A virus, and a simultaneous detection of the novel coronavirus and the influenza B virus is needed, thereby reducing costs.

In one specific embodiment, the composition includes the novel coronavirus 2019-nCOV forward primer as shown in SEQ ID NO: 1, the novel coronavirus 2019-nCOV reverse primer as shown in SEQ ID NO: 2, and the novel coronavirus 2019-nCOV probe as shown in SEQ ID NO: 3;

the influenza A virus forward primer as shown in SEQ ID NO: 7, the influenza A virus reverse primer as shown in SEQ ID NO: 8, and the influenza A virus probe as shown in SEQ ID NO: 9; and the influenza B virus forward primer as shown in SEQ ID NO: 10, the influenza B virus reverse primer as shown in SEQ ID NO: 11, and the influenza B virus probe as shown in SEQ ID NO: 12.

The above embodiment is used when there is a need to detect the three viruses, and may more comprehensively detect the virus that causes the infection, and a set of primers is used for each virus, thereby reducing costs.

In one specific embodiment, the composition includes the novel coronavirus 2019-nCOV forward primer as shown in SEQ ID NO: 1, the novel coronavirus 2019-nCOV reverse primer as shown in SEQ ID NO: 2, and the novel coronavirus 2019-nCOV probe as shown in SEQ ID NO: 3;

the novel coronavirus 2019-nCOV forward primer as shown in SEQ ID NO: 4, the novel coronavirus 2019-nCOV reverse primer as shown in SEQ ID NO: 5, and the novel coronavirus 2019-nCOV probe as shown in SEQ ID NO: 6;

the influenza A virus forward primer as shown in SEQ ID NO: 7, the influenza A virus reverse primer as shown in SEQ ID NO: 8, and the influenza A virus probe as shown in SEQ ID NO: 9; and the influenza B virus forward primer as shown in SEQ ID NO: 10, the influenza B virus reverse primer as shown in SEQ ID NO: 11, and the influenza B virus probe as shown in SEQ ID NO: 12.

The above embodiment is used when there is a need to detect the three viruses and high detection accuracy is required, and may obtain high detection accuracy and avoid false negatives.

The virus that causes the respiratory tract infection includes: the novel coronavirus 2019-nCoV, the influenza A virus, and the influenza B virus.

Further, the composition includes: an internal standard forward primer, an internal standard reverse primer, and an internal standard probe for monitoring.

In one specific embodiment, the composition further includes: the internal standard forward primer as shown in SEQ ID NO: 13, the internal standard reverse primer as shown in SEQ ID NO: 14, and the internal standard probe as shown in SEQ ID NO: 15.

In the present invention, the fluorescent reporter group may be selected from carboxyfluorescein (FAM®), hexachlorofluorescein (HEX®), carboxy-X-rhodamine (ROX®), 2'-chloro-7'-phenyl-1,4-dichloro-6-carboxyfluorescein (VIC®), cyanine 5 (CY5®), 5-carboxytetramethylrhodamine (5-TAMRA®), tetrachlorofluorescein (TET®), cyanine 3 (CY3®), and 4',5'-dichloro-2',7'-dimethoxy-5 (6)-carboxyfluorescein (JOE®), but is not limited thereto.

In one specific embodiment, fluorescent reporter groups of the novel coronavirus 2019-nCOV probes as shown in SEQ ID NOs: 3 and 6 are FAM®; a fluorescent reporter group of the influenza A virus probe as shown in SEQ ID NO: 9 is HEX®; and a fluorescent reporter group of the influenza B virus probe as shown in SEQ ID NO: 12 is ROX®.

In one specific embodiment, a fluorescent reporter group of the internal standard probe as shown in SEQ ID NO: 15 is CY5®.

Further, an amount of the primer in the composition is 50-150 nM, and an amount of the probe in the composition is 25-75 nM.

In one specific embodiment, the components of the composition of the present invention are in the same package.

Further, the components of the composition of the present invention are present in a mixed form.

In a second aspect, provided in the present application is a use of the above composition of the present invention in the preparation of a kit for detecting and typing viruses that cause the respiratory tract infection.

The virus that causes the respiratory tract infection includes: the novel coronavirus 2019-nCoV, the influenza A virus, and the influenza B virus.

In a third aspect, provided in the present application is a kit for detecting and typing viruses that cause the respiratory tract infection, the kit including the above composition of the present invention.

Further, the kit further includes at least one of a nucleic acid release reagent, a dNTP, a reverse transcriptase, a DNA polymerase, a PCR buffer, and $Mg^{2+}$.

Further, the amount of the primer in the composition is 50-150 nM; the amount of the probe in the composition is 25-75 nM; and the amount of the dNTP is 0.2-0.3 mM.

Further, a concentration of the reverse transcriptase is 5 U/μL to 15 U/μL, and for example, the reverse transcriptase may be a murine leukemia reverse transcriptase (MMLV). A concentration of the DNA polymerase is 5 U/μL to 15 U/μL, and for example, the DNA polymerase may be a Taq enzyme.

In one specific embodiment, in addition to the above composition of the present invention, the kit further includes the following components and amounts:

| Component | Volume/concentration in each reaction |
|---|---|
| $Mg^{2+}$ | 4 mM |
| dNTPs (100 mM) | 0.25 mM |
| MMLV (10 U/μL) | 10 U |
| Taq enzyme (5 U/μL) | 5 U |
| PCR buffer (1.5×) | Make up to 50 μL |

In a fourth aspect, a method for detecting and typing viruses that cause the respiratory tract infection is provided, the method including the steps of:

1) releasing a nucleic acid of a testing sample;
2) performing, by using the above composition of the present invention or the above kit of the present invention, a fluorescent quantitative PCR on the nucleic acid obtained in step 1); and
3) obtaining and analyzing results.

In the present application, the testing sample may be a throat swab, sputum, a bronchoalveolar lavage fluid, blood, etc., but is not limited thereto.

Further, reaction conditions of the fluorescent quantitative PCR are as follows:

reverse transcription at a temperature of 50 °C for 25-35 minutes for 1 cycle; pre-denaturation at a temperature of 94 °C for 2-10 minutes for 1 cycle; denaturation at a temperature of 94 °C for 10-20 seconds; annealing at a temperature of 60 °C for 20-40 seconds for 45-50 cycles.

Using the composition of the present invention may simultaneously detect and type the three viruses that cause respiratory tract infections, so as to identify some patients having fever caused by common seasonal influenza, reduce the waste of medical resources, and reduce the psychological burden on patients and society.

Furthermore, the present application may quickly diagnose the novel coronavirus 2019-nCOV, provide molecular evidence for early diagnosis, early treatment, and early isolation of the novel coronavirus, and allow adequate preparations for prevention and control of the disease, making it possible to control the source of infection of the highly contagious and hazardous novel coronavirus 2019-nCOV in a timely manner and stop virus pandemics and outbreaks.

The composition of the present invention in combination with a fluorescent probe method enables the use of one tube in one test simultaneously, achieving low costs and high throughput. The present application enables information of four targets to be given by one tube in a single test, and the operations are simple and convenient, and a result reading process may be completed according to a CT value. The whole detection process is carried out under single-tube closed conditions, avoiding false positives and environmental contamination caused by crossover between samples.

Additionally, using the composition of the present invention is time-efficient, and the total time from acquiring a sample to obtaining a result is about 120 min, greatly improving the detection efficiency.

DETAILED DESCRIPTION

Figure 1:
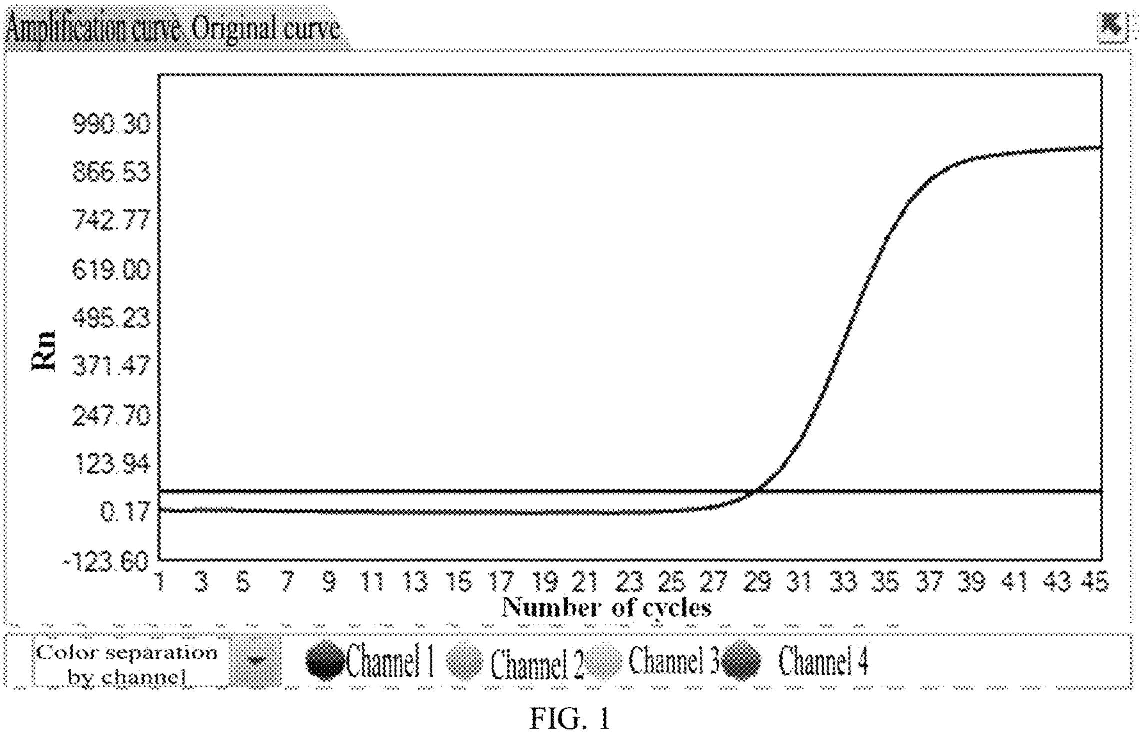
FIG. 1 shows a positive detection result for 2019-nCOV in a FAM® channel of the composition of the present invention.
Figure 2:
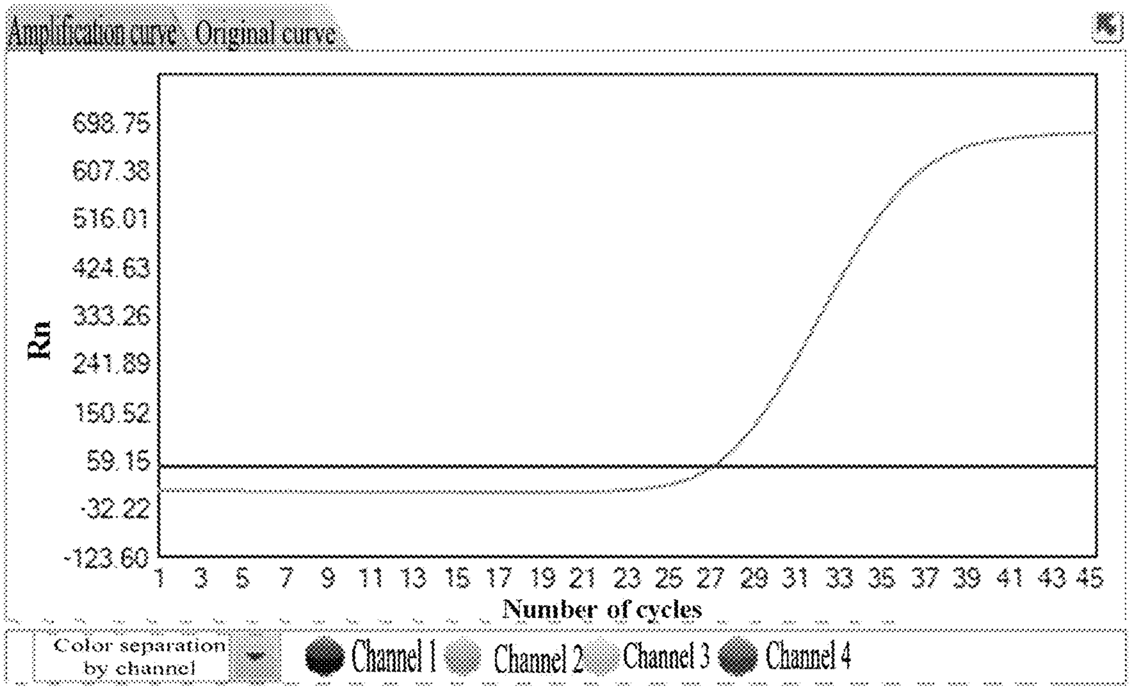
FIG. 2 shows a positive detection result for influenza A virus in a HEX® channel of the composition of the present invention.
Figure 3:
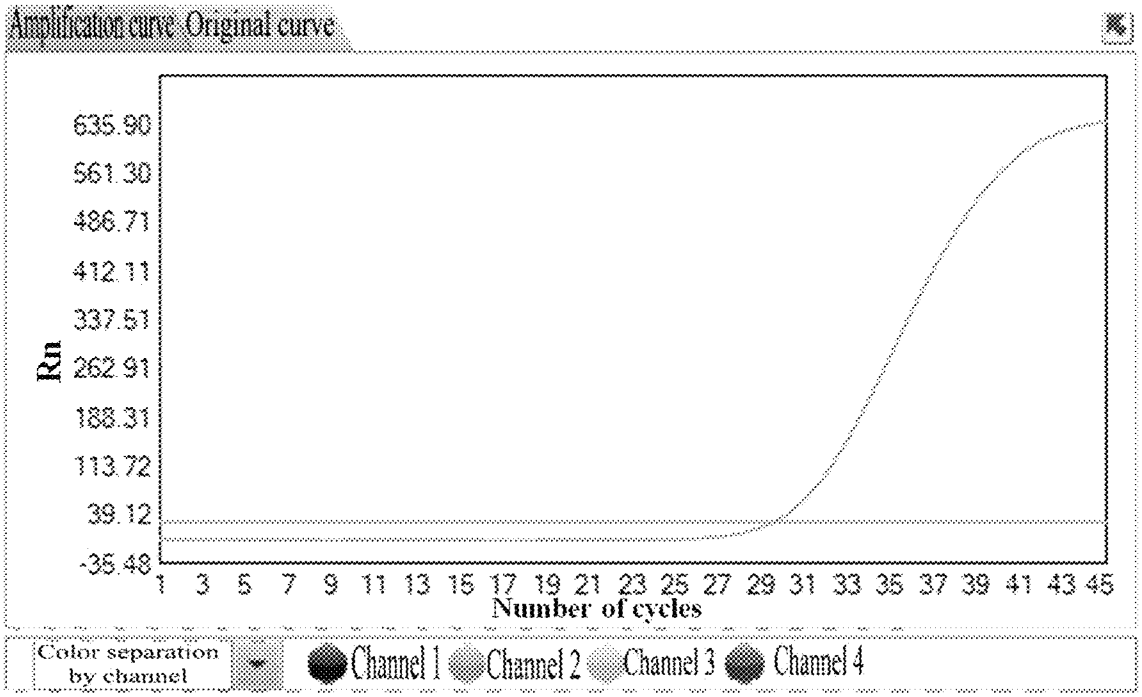
FIG. 3 shows a positive detection result for influenza B virus in a ROX® channel of the composition of the present invention.
Figure 4:
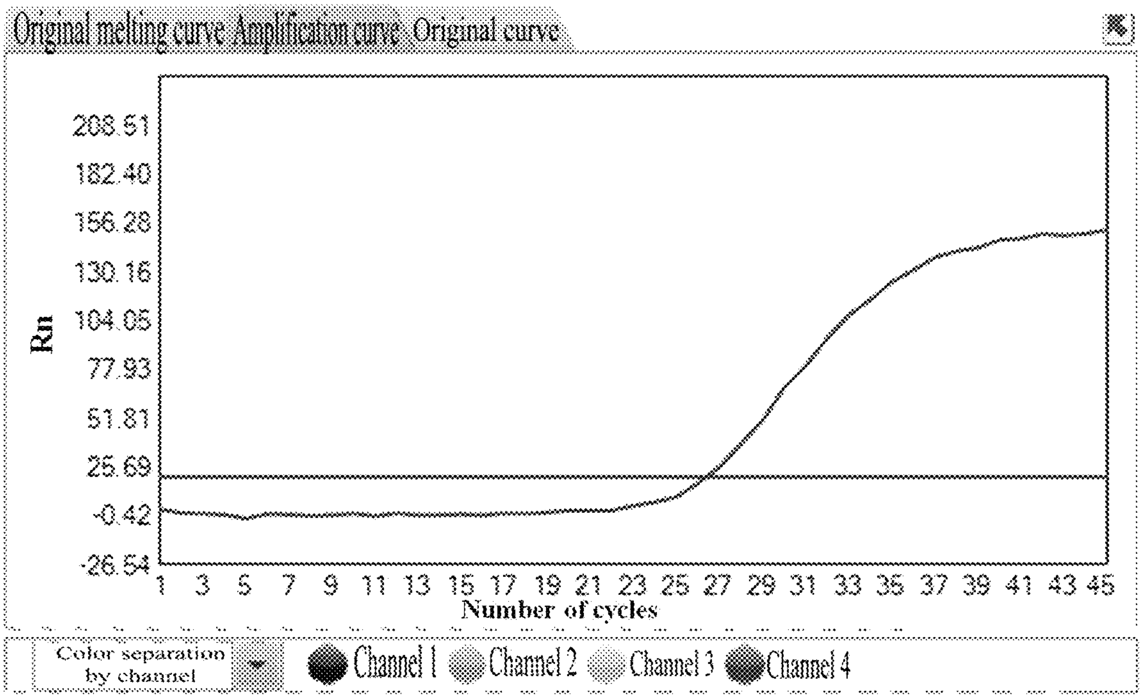
FIG. 4 shows a positive detection result for an internal standard in a CY5® channel of the composition of the present invention.
Figure 5:
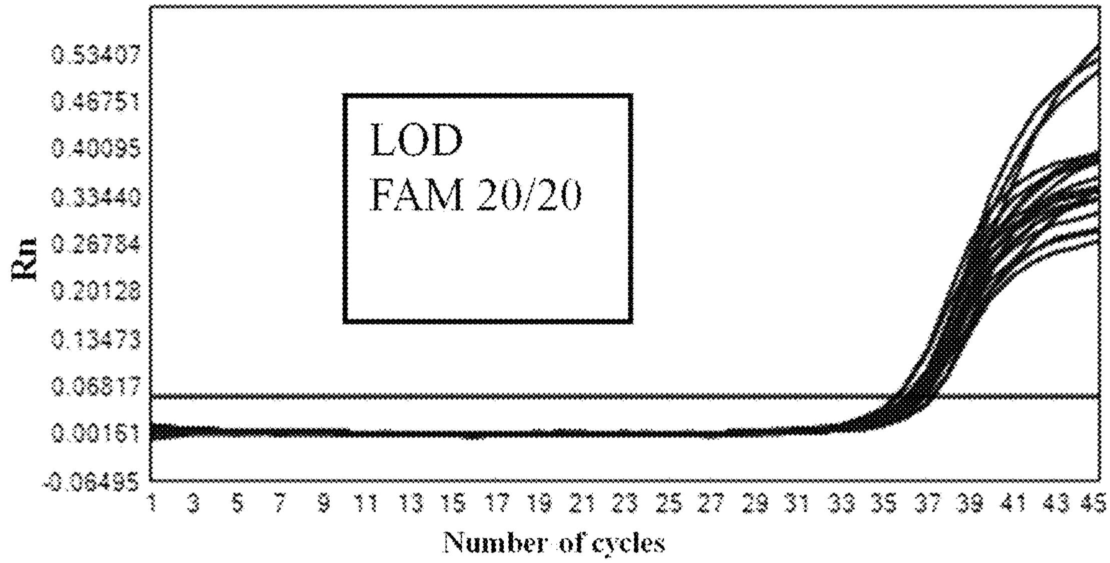
FIGS. 5-8 show reproducibility results of virus detection according to an embodiment of the composition of the present invention.
Figure 6:
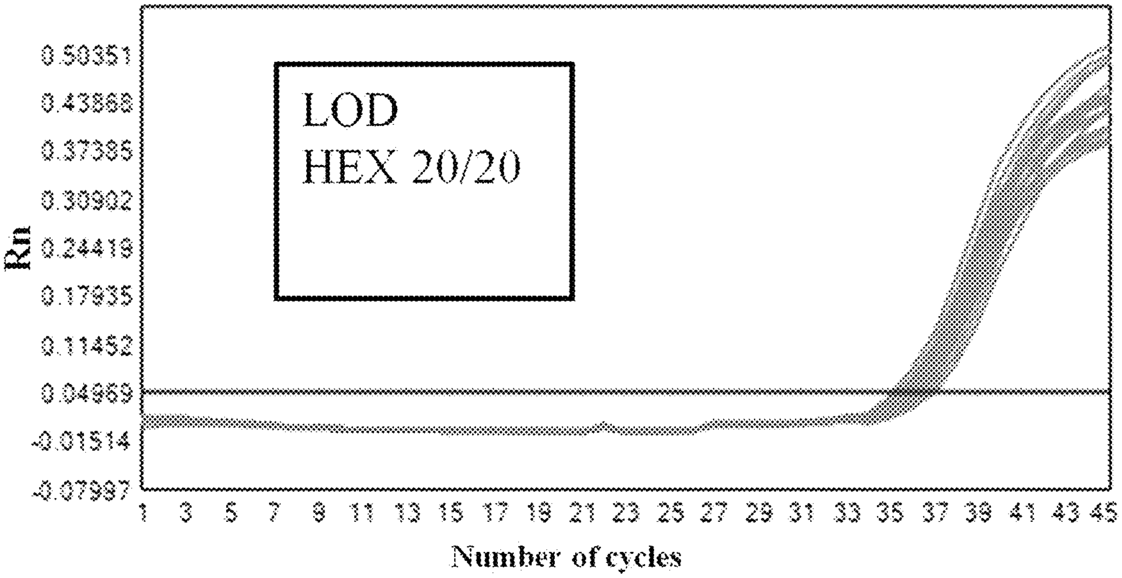
Figure 7:
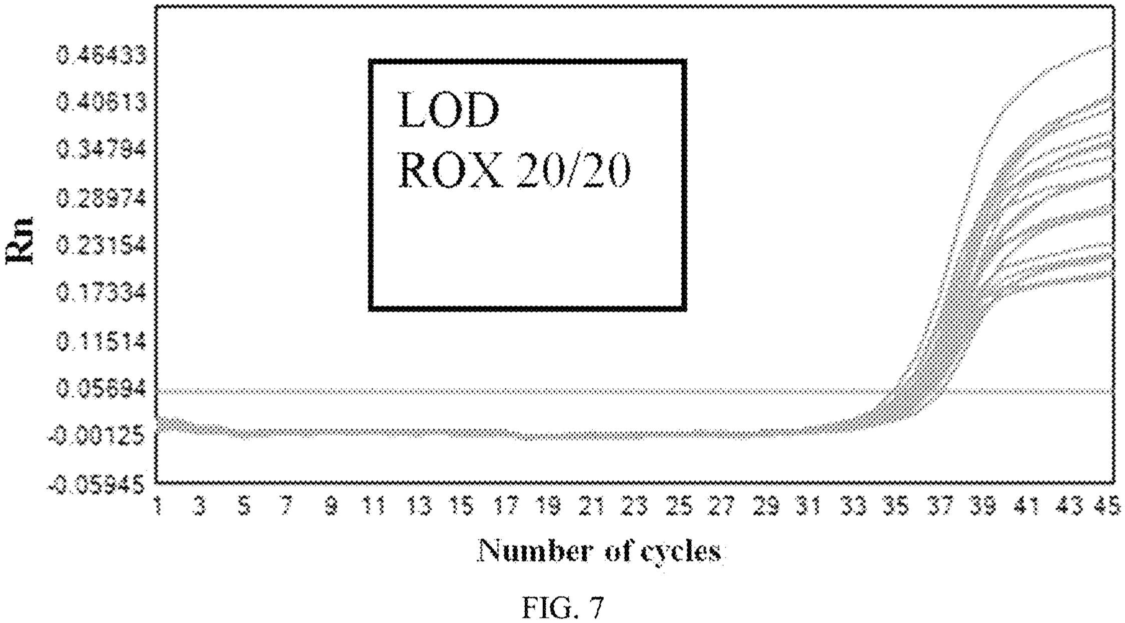
Figure 8:
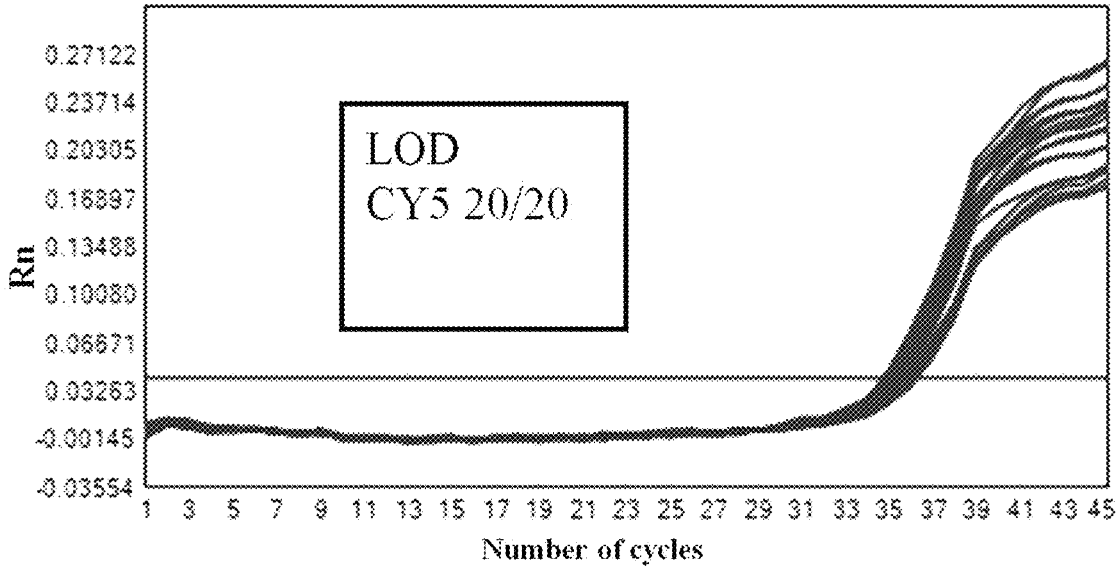
Figure 9:
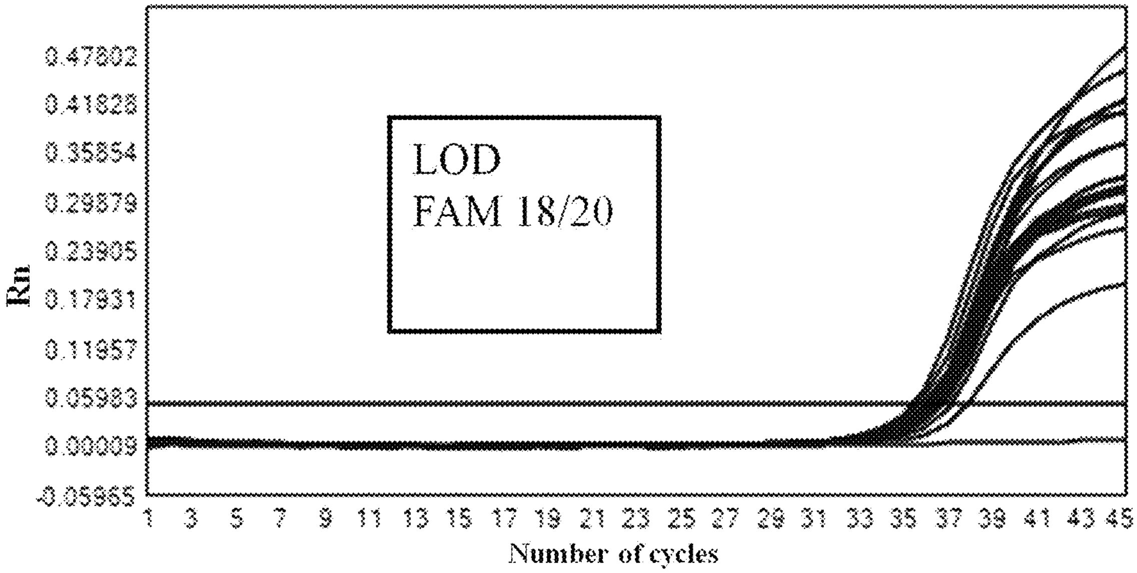
FIGS. 9-12 show reproducibility results of virus detection according to another embodiment of the composition of the present invention.
Figure 10:
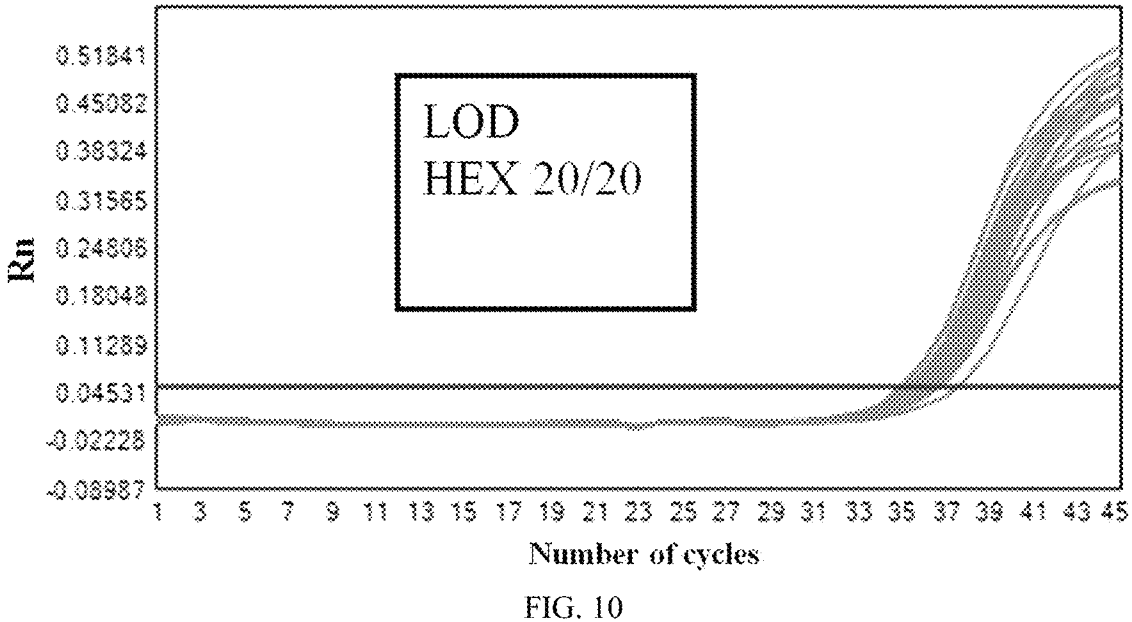
Figure 11:
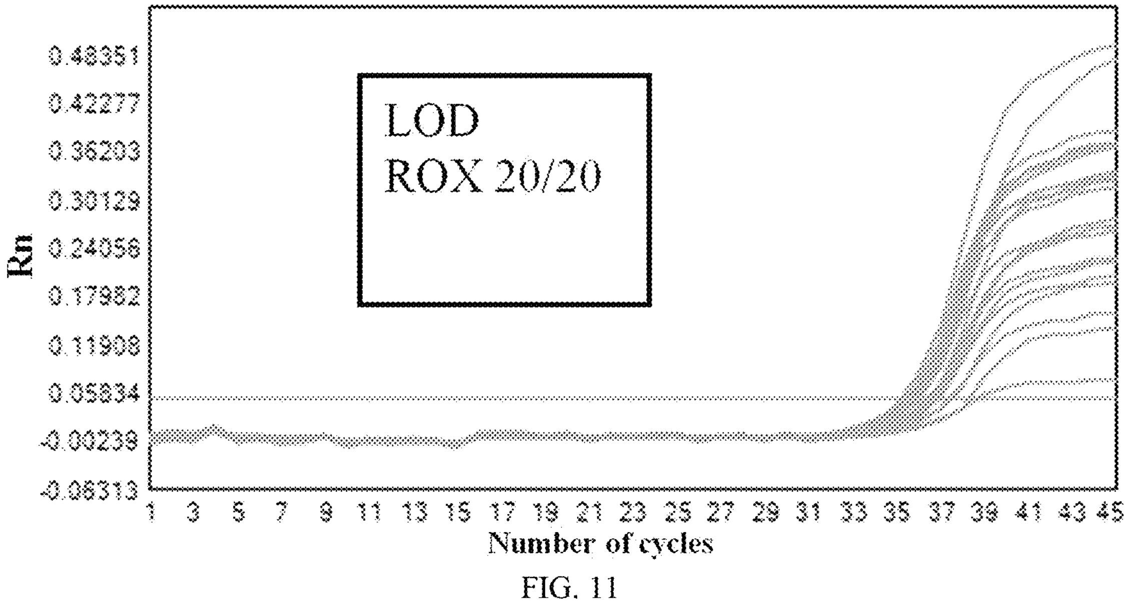
Figure 12:
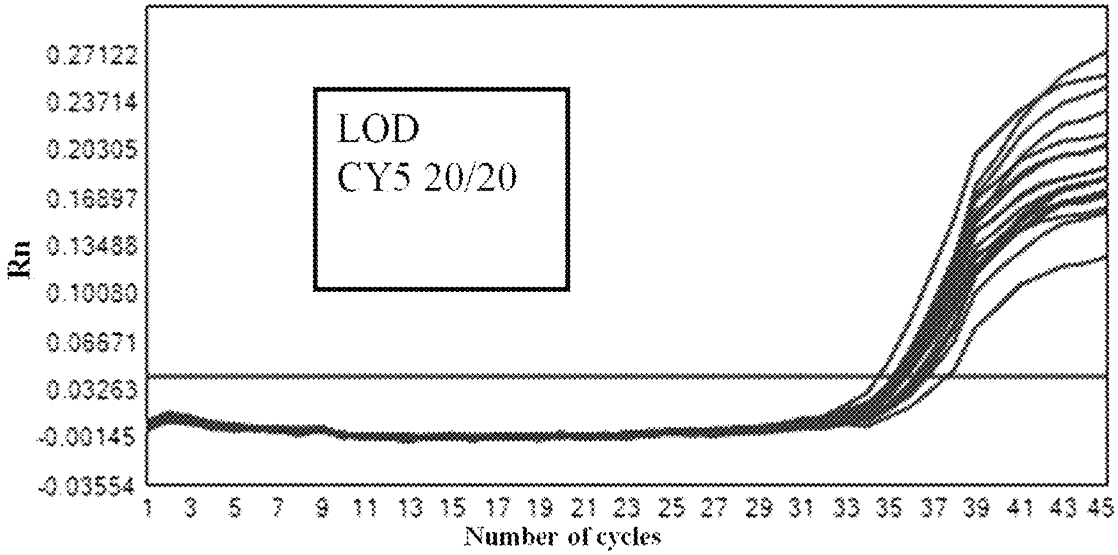

The present invention will be described in detail below with reference to specific embodiments and examples, and the advantages and various effects of the present invention will be more clearly presented therefrom. It should be understood by those skilled in the art that these specific embodiments and examples are intended to illustrate the present invention, rather than to limit the present invention.

Example 1. Primers and Probes Used in the Present Invention

The primers and probes used in the present invention are shown in Table 1 below:

TABLE 1

| | |
|---|---|
| Novel coronavirus 2019-nCoV forward primer (ORF1ab) (SEQ ID NO: 1) | TGTAGCTTGTCACACCGTTT |
| Novel coronavirus 2019-nCoV reverse primer (ORF1ab) (SEQ ID NO: 2) | ATTAGCATAAGCAGTTGTGGCAT |

TABLE 1-continued

| | |
|---|---|
| Novel coronavirus 2019-nCoV probe (ORF1ab) (SEQ ID NO: 3) | ATAGTGAACCGCCACACATGACCA |
| Novel coronavirus 2019-nCoV forward primer (N) (SEQ ID NO: 4) | CTCACTCAACATGGCAAGG |
| Novel coronavirus 2019-nCoV reverse primer (N) (SEQ ID NO: 5) | ACTGAGATCTTTCATTTTACCGTCAC |
| Novel coronavirus 2019-nCoV probe (N) (SEQ ID NO: 6) | CTACTACCGAAGAGCTACCAGACGAA |
| Influenza A virus forward primer (SEQ ID NO: 7) | GTATTACTAAGGGCTTTCACCGA |
| Influenza A virus reverse primer (SEQ ID NO: 8) | ATTCCATTCAAGTCCTCCGATG |
| Influenza A virus probe (SEQ ID NO: 9) | AAAAGAAGGCAATGGTGAGATTTCGC |
| Influenza B virus forward primer (SEQ ID NO: 10) | GAGCTGCCTATGAAGACCTGA |
| Influenza B virus reverse primer (SEQ ID NO: 11) | GCTCCCATTCCTTCTACCTG |
| Influenza B virus probe (SEQ ID NO: 12) | TTTGCTGGAACATGGAAACCCTT |
| Internal standard forward primer (SEQ ID NO: 13) | TTTGGTATCGTGGAAGGACTCA |
| Internal standard reverse primer (SEQ ID NO: 14) | GCCATCACGCCACAGTTTC |
| Internal standard probe (SEQ ID NO: 15) | ACCACAGTCCATGCCATCACTGCC |

Among them, a fluorescent reporter group of the novel coronavirus 2019-nCOV probe was FAM®; a fluorescent reporter group of an influenza A virus was HEX®; a fluorescent reporter group of an influenza B virus was ROX®, a fluorescent reporter group of the internal standard was CY5®, and the 3'-end of the probe further had a BHQ1® or BHQ2® quencher group.

Example 2. Method for Detecting and Typing Viruses that Cause a Respiratory Tract Infection A testing sample of the present invention was a throat swab, sputum, a bronchoalveolar lavage fluid, or blood. A magnetic bead method was used to extract a viral nucleic acid, and the following operations were performed in a sample processing room:

2.1 An appropriate number of 1.5-mL sterilized centrifuge tubes were taken, and labeled as a negative control, a positive control, and a testing sample, respectively. 300 μL of an RNA extraction solution 1 was added to each tube.

2.2 200 μL of the testing sample or the negative control or the positive control was added to each tube. The tube was covered with a cap, and shaken for 10 seconds for through mixing, and subjected to instant centrifugation.

2.3 100 μL of an RNA extraction solution 2-mix was added to each tube (sucked up after through mixing), and the tube was shaken for 10 seconds for through mixing, and left to stand for 10 minutes at room temperature.

2.4 After instant centrifugation, the centrifuge tubes were placed on a separator, and the solution was slowly sucked out after 3 minutes (be careful not to touch a brown substance adhered to the tube wall).

2.5 600 μL of an RNA extraction solution 3 and 200 μL of an RNA extraction solution 4 were added to each tube, and the tube was shaken for 5 seconds for through mixing and subjected to instant centrifugation, and then the centrifuge tube was placed on the separator again.

2.6 After about 3 minutes, the supernatant separated into two layers. A pipette tip was inserted into the bottom of the centrifuge tube, the liquid was slowly sucked up from the bottom completely and discarded. The tube was left to stand for 1 minute and then the residual liquid at the bottom of the tube was completely sucked up and discarded.

2.7 50 μL of PCR-mix was added to each tube, and a pipette tip was used to suck up the PCR-mix to elute the brown residue adhered to the wall of the centrifuge tube. The operation was repeated several times to elute the residue as completely as possible, and then all the eluted brown mixture was transferred to a 0.2-mL PCR reaction tube, and the tube was covered with a cap and transferred to an amplification test zone.

The real-time fluorescent PCR reaction system was configured as follows:

| Component | Volume/concentration in each reaction |
|---|---|
| $Mg^{2+}$ | 4 mM |
| dNTPs (100 mM) | 0.25 mM |
| MMLV (10 U/μL) | 10 U |
| Taq enzyme (5 U/μL) | 5 U |
| Primer | 100 nM |
| Probe | 50 nM |
| PCR buffer (1.5×) | Make up to 50 μL |

The PCR amplification program was set up as follows:

| Step | Temperature | Time | Number of cycles |
|---|---|---|---|
| Reverse transcription | 50 °C | 30 minutes | 1 |
| Pre-denaturation | 94 °C | 5 minutes | 1 |
| Denaturation | 94 °C | 15 seconds | 45 |
| Annealing | 60 °C | 30 seconds | |

Results Analysis:

1) Target detection signals were FAM®, HEX® (or VIC®), and ROX®, and an internal reference detection signal was CY5®.

2) Baseline setting: The baseline was generally set to 3-15 cycles, which specifically could be adjusted according to actual situations. The adjustment principle was to select a region where a fluorescence signal was relatively stable before exponential amplification, a starting point (Start) avoiding signal fluctuation in an initial stage of fluorescence collection, and an ending point (End) being less by 1-2 cycles than the Ct of a sample showing earliest exponential amplification. Threshold setting: The setting principle was to make a threshold line just exceed the highest point of a normal negative control.

3) It was first analyzed whether an amplification curve for the internal standard was detected in the CY5 channel and Ct≤39, and if so, it indicated that the current test was effective, and subsequent analysis continued to be carried out:

A) if a typical S-shaped amplification curve was detected in the FAM® channel and Ct<39, it indicated that the novel coronavirus 2019-nCOV detection result was positive;

B) if a typical S-type amplification curve was detected in the HEX® channel and Ct<39, it indicated that the influenza A virus detection result was positive;

C) if a typical S-type amplification curve was detected in the ROX® channel and Ct<39, it indicated that the influenza B detection result was positive.

4) If a Ct for the internal standard was not detected in the CY5® channel or Ct>39, it indicated that the concentration of the testing sample was excessively low or there was an interfering substance that inhibited the reaction, and the experiment needed to be re-prepared.

Example 3. Detection Results of Detecting the Positive Control by the Composition of the Present Invention The composition in Table 1 of the present invention was used to detect each target-positive plasmid according to the method described in Example 2, so as to simulate a clinical sample. Multiple PCR tests were conducted on a Hongshi fluorescent quantitative PCR instrument. The results are as shown in FIGS. 1-4. A good amplification curve could be detected in each channel, indicating that the composition of the present invention could detect and type viruses that cause the respiratory tract infection.

Example 4. Reproducibility Results of Detecting the Positive Control by Different Compositions of the Present Invention The composition in Table 1 of the present invention was used to detect each target LOD (sensitivity)-positive plasmid according to the method described in Example 2, so as to simulate a clinical sample. Multiple PCR tests were conducted on a Hongshi fluorescent quantitative PCR instrument. The results of this combination are the most desirable, and the virus could be detected in all 20 repetitions, as shown in FIGS. 5-8.

Experiments were carried out using only one set of primers targeting the novel coronavirus (i.e., using only SEQ ID NOs: 1-3) in combination with the primers for the influenza A virus and the influenza B virus. The results of this combination were that the virus could be detected in the HEX®, ROX®, and CY5® channels in all 20 repetitions, and the virus could be detected in the FAM® channel in 18 of 20 repetitions. The results are shown in FIGS. 9-12.

Example 5. Sensitivity of the Composition of the Present Invention

Figure 13:
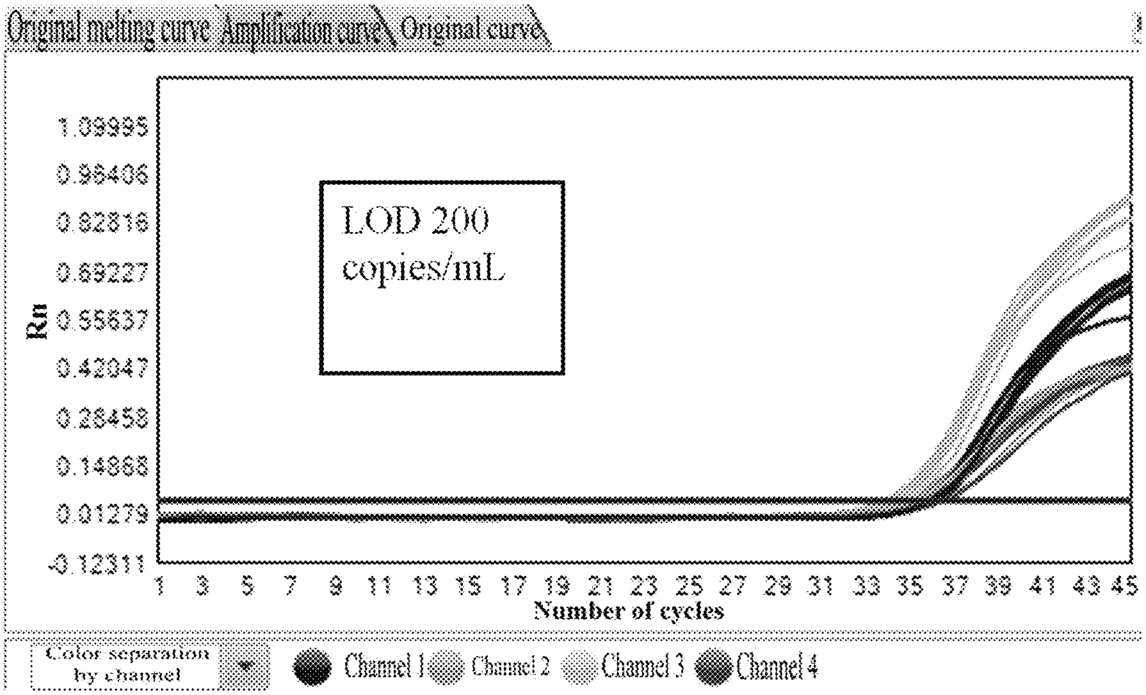
FIG. 13 shows sensitivity results of the composition of the present invention.

Experiments were carried out with plasmid templates of different concentrations to test the sensitivity of the composition of the present invention The composition in Table 1 of the present invention was used to detect each target LOD (sensitivity)-positive plasmid according to the method described in Example 2, so as to simulate a clinical sample. Multiple PCR tests were conducted on a Hongshi fluorescent quantitative PCR instrument. The detection sensitivity in each channel was 200 copies/mL. The results show that the composition of the present invention could still detect a virus at a concentration of 200 copies/mL. The results are as shown in FIG. 13, indicating that the sensitivity of the composition of the present invention could reach 200 copies/mL.

Example 6. Specificity of the Composition of the Present Invention

Figure 14:
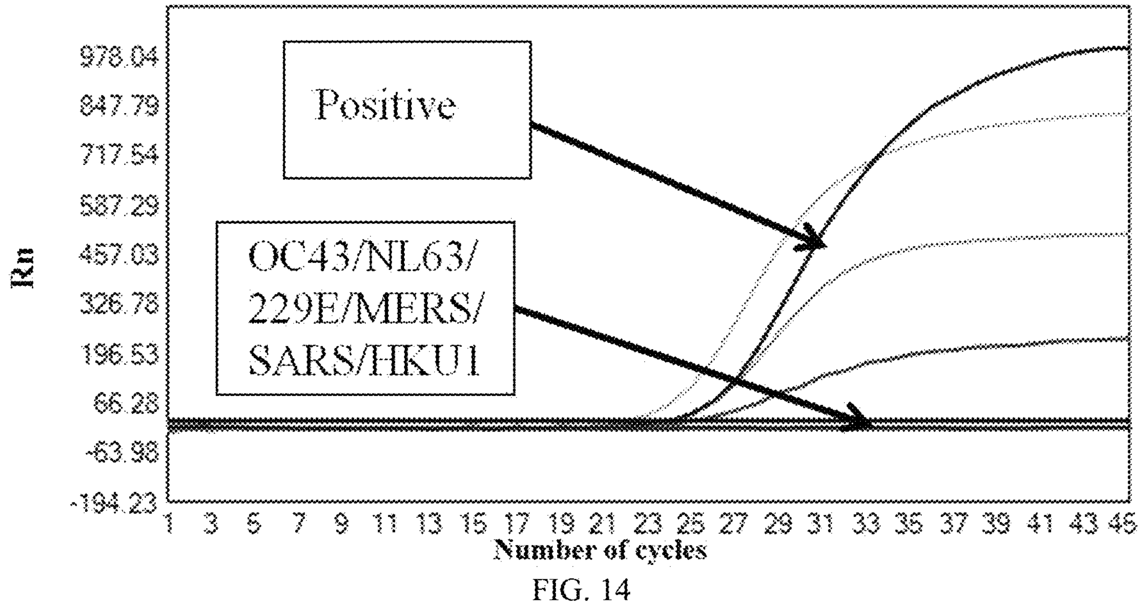
FIGS. 14-15 show specificity results of the composition of the present invention.
Figure 15:
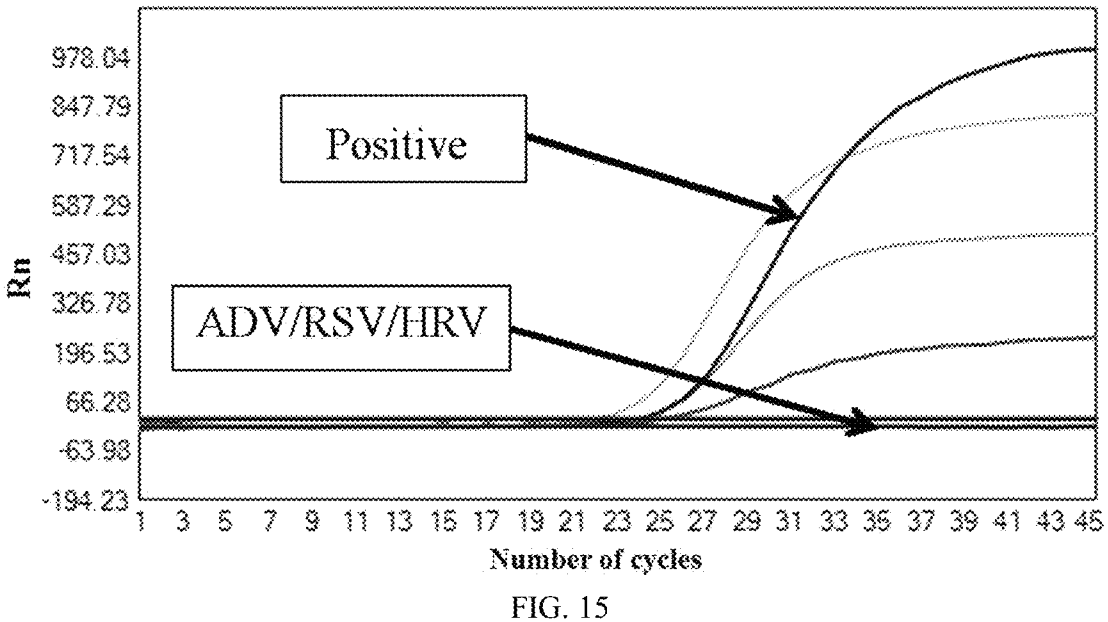

Experiments with some similar viruses showed that the composition of the present invention would not detect other viruses and cause false positives. The results are as shown in FIGS. 14-15, in which the composition of the present invention showed no non-specific amplification to other coronaviruses OC43/OC43/NL63/229E/MERS/SARS/HKU1 as well as common viruses adenovirus ADV, syncytial virus RSV, rhinovirus HRV, indicating that the composition of the present invention has good specificity.

Comparative Example 1. Other Primers and Probes Designed by the Present Invention with Poor Effects In the process of primer and probe design, the inventor also designed other primers and probes for virus detection, and specific sequences thereof were as follows (all targets are ORF-lab):

```
F1 (SEQ ID NO: 16):
CCCCAAAATGCTGTTGTTAAAATT

R1 (SEQ ID NO: 17):
TTCAAGCCAGATTCATTATGGTATT

P1 (SEQ ID NO: 18):
FAM®-TCCAGCATGTCACAATTCAGAAGTAGGAC-BHQ1

F2 (SEQ ID NO: 19):
CCCGCACTCTTGAAACTGCTC

R2 (SEQ ID NO: 20):
TAGATTGTTAGTAGCCAAATCAGATGTG
```

-continued

```
P2 (SEQ ID NO: 21):
FAM®-CTGTGCGTGTTTTACAGAAGGCCGC-BHQ1®

F3 (SEQ ID NO: 22):
GTTGCTCGAAATCAAAGACACAGAA

R3 (SEQ ID NO: 23):
CTTGTAACCTTGCACTTCTATCACAGT

P3 (SEQ ID NO: 24):
FAM®-TTGCACCTAATATGATGGTAACAAACAATACCT-BHQ1®
```

Figure 16:
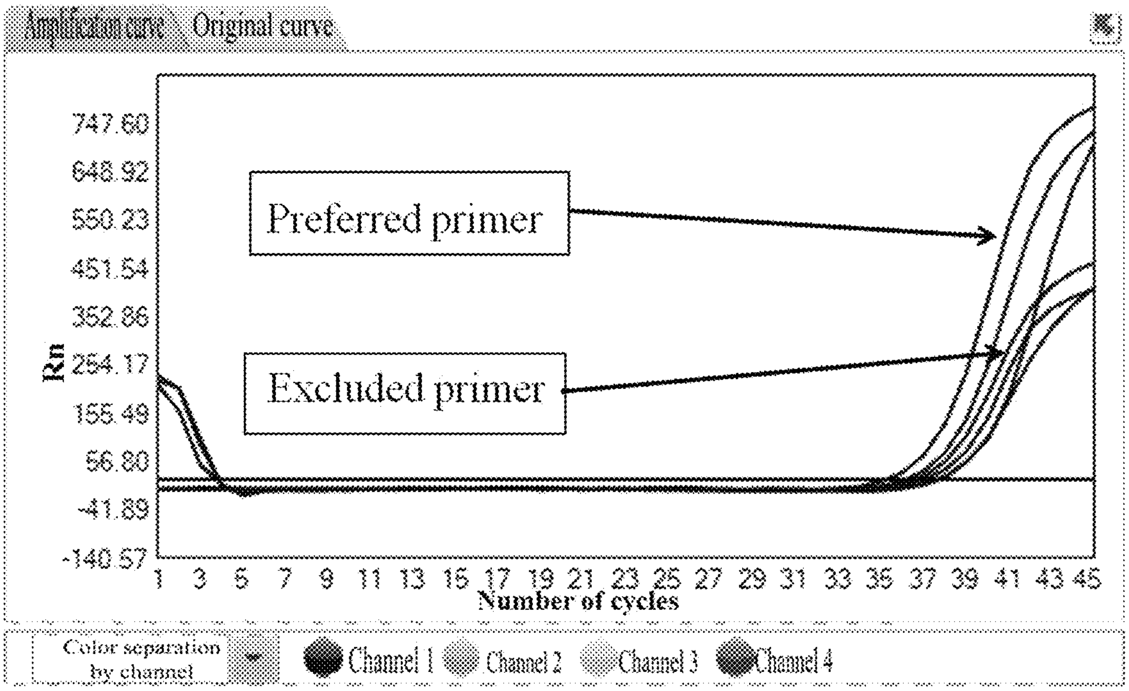
FIG. 16 shows experimental results of the composition of the present invention and a comparative primer.

The above composition was used for detection according to the method shown in Example 2. As can be seen from FIG. 16, the primers of the comparative example could not desirably detect positive plasmids, which proved that the primers of the comparative example could not be used to detect viruses that cause the respiratory tract infection.

REFERENCE TO AN ELECTRONIC SEQUENCE LISTING

The contents of the electronic sequence listing (CU704SequenceListing.xml; Size: 27,083 bytes; and Date of Creation: Sep. 19, 2022) is herein incorporated by reference in its entirety.

What is claimed is:

1. A composition capable of detecting and typing viruses that cause a respiratory tract infection, the composition consisting of:

a coronavirus 2019-nCOV forward primer consisting of the nucleic acid sequence of SEQ ID NO: 1, a coronavirus 2019-nCOV reverse primer consisting of the nucleic acid sequence of SEQ ID NO: 2, and a coronavirus 2019-nCOV probe consisting of the nucleic acid sequence of SEQ ID NO: 3; and at least one of the following two groups:

a first group: an influenza A virus forward primer consisting of the nucleic acid sequence of SEQ ID NO: 7, an influenza A virus reverse primer consisting of the nucleic acid sequence of SEQ ID NO: 8, and an influenza A virus probe consisting of the nucleic acid sequence of SEQ ID NO: 9; and a second group: an influenza B virus forward primer consisting of the nucleic acid sequence of SEQ ID NO: 10, an influenza B virus reverse primer consisting of the nucleic acid sequence of SEQ ID NO: 11, and an influenza B virus probe consisting of the nucleic acid sequence of SEQ ID NO: 12; and the coronavirus 2019-nCOV probe is labeled with a fluorescent reporter group at the 5' end; the influenza A virus probe is labeled with a fluorescent reporter group at the 5' end; the influenza B virus probe is labeled with a fluorescent reporter group at the 5' end;

wherein fluorescent reporter groups of the coronavirus 2019-nCOV probe, influenza A virus probe and influenza B virus probe are different from each other and do not interfere with each other.

2. A composition capable of detecting and typing viruses that cause a respiratory tract infection, the composition consisting of:

a coronavirus 2019-nCOV forward primer consisting of the nucleic acid sequence of SEQ ID NO: 1, a coronavirus 2019-nCOV reverse primer consisting of the nucleic acid sequence of SEQ ID NO: 2, and a coronavirus 2019-nCOV probe consisting of the nucleic acid sequence of SEQ ID NO: 3; and at least one of the following two groups:

a first group: an influenza A virus forward primer consisting of the nucleic acid sequence of SEQ ID NO: 7, an influenza A virus reverse primer consisting of the nucleic acid sequence of SEQ ID NO: 8, and an influenza A virus probe consisting of the nucleic acid sequence of SEQ ID NO: 9; and a second group: an influenza B virus forward primer consisting of the nucleic acid sequence of SEQ ID NO: 10, an influenza B virus reverse primer consisting of the nucleic acid sequence of SEQ ID NO: 11, and an influenza B virus probe consisting of the nucleic acid sequence of SEQ ID NO: 12; and a coronavirus 2019-nCOV forward primer consisting of the nucleic acid sequence of SEQ ID NO: 4, a coronavirus 2019-nCOV reverse primer consisting of the nucleic acid sequence of SEQ ID NO: 5, and a coronavirus 2019-nCOV probe consisting of the nucleic acid sequence of SEQ ID NO: 6; and the coronavirus 2019-nCOV probe is labeled with a fluorescent reporter group at the 5' end; the influenza A virus probe is labeled with a fluorescent reporter group at the 5'; the influenza B virus probe is labeled with a fluorescent reporter group at the 5' end;

wherein fluorescent reporter groups of the coronavirus 2019-nCOV probe, influenza A virus probe and influenza B virus probe are different from each other and do not interfere with each other.

3. The composition according to claim 1, wherein the composition consisting of:

the coronavirus 2019-nCOV forward primer consisting of the nucleic acid sequence of SEQ ID NO: 1, the coronavirus 2019-nCOV reverse primer consisting of the nucleic acid sequence of SEQ ID NO: 2, and the coronavirus 2019-nCOV probe consisting of the nucleic acid sequence of in SEQ ID NO: 3; and the influenza A virus forward primer consisting of the nucleic acid sequence of SEQ ID NO: 7, the influenza A virus reverse primer consisting of the nucleic acid sequence of SEQ ID NO: 8, and the influenza A virus probe consisting of the nucleic acid sequence of SEQ ID NO: 9.

4. The composition according to claim 1, wherein the composition consisting of:

the coronavirus 2019-nCOV forward primer consisting of the nucleic acid sequence of SEQ ID NO: 1, the coronavirus 2019-nCOV reverse primer consisting of the nucleic acid sequence of SEQ ID NO: 2, and the coronavirus 2019-nCOV probe consisting of the nucleic acid sequence of SEQ ID NO: 3; and the influenza B virus forward primer consisting of the nucleic acid sequence of SEQ ID NO: 10, the influenza B virus reverse primer consisting of the nucleic acid sequence of SEQ ID NO: 11, and the influenza B virus probe consisting of the nucleic acid sequence of SEQ ID NO: 12.

5. The composition according to claim 1, wherein the composition consisting of:

the coronavirus 2019-nCOV forward primer consisting of the nucleic acid sequence of SEQ ID NO: 1, the coronavirus 2019-nCOV reverse primer consisting of the nucleic acid sequence of SEQ ID NO: 2, and the coronavirus 2019-nCOV probe consisting of the nucleic acid sequence of SEQ ID NO: 3;

the influenza A virus forward primer consisting of the nucleic acid sequence of SEQ ID NO: 7, the influenza A virus reverse primer consisting of the nucleic acid sequence of SEQ ID NO: 8, and the influenza A virus probe consisting of the nucleic acid sequence of SEQ ID NO: 9; and the influenza B virus forward primer consisting of the nucleic acid sequence of SEQ ID NO: 10, the influenza B virus reverse primer consisting of the nucleic acid sequence of SEQ ID NO: 11, and the influenza B virus probe consisting of the nucleic acid sequence of SEQ ID NO: 12.

6. The composition according to claim 2, wherein the composition consisting of:

the coronavirus 2019-nCOV forward primer consisting of the nucleic acid sequence of SEQ ID NO: 1, the coronavirus 2019-nCOV reverse primer consisting of the nucleic acid sequence of SEQ ID NO: 2, and the coronavirus 2019-nCOV probe consisting of the nucleic acid sequence of SEQ ID NO: 3;

the coronavirus 2019-nCOV forward primer consisting of the nucleic acid sequence of SEQ ID NO: 4, the coronavirus 2019-nCOV reverse primer consisting of the nucleic acid sequence of SEQ ID NO: 5, and the coronavirus 2019-nCOV probe consisting of the nucleic acid sequence of SEQ ID NO: 6;

the influenza A virus forward primer consisting of the nucleic acid sequence of SEQ ID NO: 7, the influenza A virus reverse primer consisting of the nucleic acid sequence of SEQ ID NO: 8, and the influenza A virus probe consisting of the nucleic acid sequence of SEQ ID NO: 9; and the influenza B virus forward primer consisting of the nucleic acid sequence of SEQ ID NO: 10, the influenza B virus reverse primer consisting of the nucleic acid sequence of SEQ ID NO: 11, and the influenza B virus probe consisting of the nucleic acid sequence of SEQ ID NO: 12.

7. A composition capable of detecting and typing viruses that cause a respiratory tract infection, the composition consisting of:

a coronavirus 2019-nCOV forward primer consisting of the nucleic acid sequence of SEQ ID NO: 1, a coronavirus 2019-nCOV reverse primer consisting of the nucleic acid sequence of SEQ ID NO: 2, and a coronavirus 2019-nCOV probe consisting of the nucleic acid sequence of SEQ ID NO: 3; and at least one of the following two groups:

a first group: an influenza A virus forward primer consisting of the nucleic acid sequence of SEQ ID NO: 7, an influenza A virus reverse primer consisting of the nucleic acid sequence of SEQ ID NO: 8, and an influenza A virus probe consisting of the nucleic acid sequence of SEQ ID NO: 9; and a second group: an influenza B virus forward primer consisting of the nucleic acid sequence of SEQ ID NO: 10, an influenza B virus reverse primer consisting of the nucleic acid sequence of SEQ ID NO: 11, and an influenza B virus probe consisting of the nucleic acid sequence of SEQ ID NO: 12; and an internal standard forward primer, an internal standard reverse primer, and an internal standard probe for monitoring; the internal standard probe is labeled with a fluorescent reporter group at the 5';

the coronavirus 2019-nCOV probe is labeled with a fluorescent reporter group at the 5' end; the influenza A virus probe is labeled with a fluorescent reporter group at the 5' end; the influenza B virus probe is labeled with a fluorescent reporter group at the 5' end;

wherein fluorescent reporter groups of the coronavirus 2019-nCOV probe, influenza A virus probe and influenza B virus probe are different from each other and do not interfere with each other.

8. The composition according to claim 7, wherein a sequence of the internal standard forward primer is consisting of the nucleic acid sequence of SEQ ID NO: 13, a sequence of the internal standard reverse primer consisting of the nucleic acid sequence of SEQ ID NO: 14, and a sequence of the internal standard probe is consisting of the nucleic acid sequence of SEQ ID NO: 15.

9. The composition according to claim 1, wherein each of the components of the composition are in the same package.

10. The composition according to claim 1, wherein the fluorescent reporter groups of the coronavirus 2019-nCOV probe, influenza A virus probe and influenza B virus probe are selected from carboxyfluorescein, hexachlorofluorescein, carboxy-x-rhodamine, 2'-chloro-7'-phenyl-1,4-dichloro-6-carboxyfluorescein, cyanine 5,5-carboxytetramethylrhodamine, tetrachlorofluorescein, cyanine 3, and 4',5'-dichloro-2',7'-dimethoxy-5(6)-carboxyfluorescein.

11. The composition according to claim 10, wherein fluorescent reporter groups of the coronavirus 2019-nCOV probes consisting of the nucleic acid sequence of SEQ ID NOs: 3 and 6 are carboxyfluorescein; a fluorescent reporter group of the influenza A virus probe consisting of the nucleic acid sequence of SEQ ID NO: 9 is hexachlorofluorescein; and a fluorescent reporter group of the influenza B virus probe consisting of the nucleic acid sequence of SEQ ID NO: 12 is carboxy-x-rhodamine.

12. The composition according to claim 7, wherein a fluorescent reporter group of the internal standard probe consisting of the nucleic acid sequence of SEQ ID NO: 15 is cyanine 5.

13. A kit for detecting and typing viruses that cause a respiratory tract infection, the kit comprising the composition according to claim 1 and instructions.

14. The kit according to claim 13, wherein the kit further comprises at least one of a nucleic acid release reagent, a dNTP, a reverse transcriptase, a DNA polymerase, a PCR buffer, and $Mg^{2+}$.

15. The kit according to claim 14, wherein an amount of each primer in the composition is 50-150 nM, and an amount of each probe in the composition is 25-75 nM.

16. The kit according to claim 14, wherein a concentration of the reverse transcriptase is 5 U/μL to 15 U/μL, and a concentration of the DNA polymerase is 5 U/μL to 15 U/μL.

17. A method for detecting and typing viruses that cause a respiratory tract infection, the method comprising the steps of:

1) Releasing a nucleic acid of a testing sample;
2) Performing, by using the composition according to claim 1, a fluorescent quantitative PCR on the nucleic acid obtained in step 1); and
3) Obtaining and analyzing results.

18. The method according to claim 17, wherein the testing sample is selected from a throat swab, sputum, bronchoalveolar lavage fluid, and blood.

19. The method according to claim 17, wherein reaction conditions of the fluorescent quantitative PCR are as follows:

reverse transcription at a temperature of 50 °C for 25-35 minutes for 1 cycle; pre-denaturation at a temperature of 94 °C for 2-10 minutes for 1 cycle; denaturation at a temperature of 94 °C for 10-20 seconds; annealing at a temperature of 60 °C for 20-40 seconds for 45-50 cycles.

20. A method for diagnosing a coronavirus 2019-nCOV, the method comprising the steps of:

1) Releasing a nucleic acid of a testing sample;
2) Performing, by using the composition according to claim 1, a fluorescent quantitative PCR on the nucleic acid obtained in step 1); and
3) Obtaining and analyzing the results, if a typical S-shaped amplification curve is detected in a fluorescent reporter groups channel of the coronavirus 2019-nCOV probe shown in SEQ ID NO:3, and Ct<39, a detection result of the coronavirus 2019-nCOV is indicated as positive.

* * * * *

SEQUENCE LISTING

```
Sequence total quantity: 24
SEQ ID NO: 1           moltype = DNA  length = 20
FEATURE                Location/Qualifiers
source                 1..20
                       mol_type = other DNA
                       note = Novel coronavirus 2019-nCoV forward primer (ORFlab)
                       organism = synthetic construct
SEQUENCE: 1
tgtagcttgt cacaccgttt                                              20

SEQ ID NO: 2           moltype = DNA  length = 23
FEATURE                Location/Qualifiers
source                 1..23
                       mol_type = other DNA
                       note = Novel coronavirus 2019-nCoV reverse primer (ORFlab)
                       organism = synthetic construct
SEQUENCE: 2
attagcataa gcagttgtgg cat                                          23

SEQ ID NO: 3           moltype = DNA  length = 24
FEATURE                Location/Qualifiers
source                 1..24
                       mol_type = other DNA
                       note = Novel coronavirus 2019-nCoV probe (ORFlab)
                       organism = synthetic construct
SEQUENCE: 3
atagtgaacc gccacacatg acca                                         24

SEQ ID NO: 4           moltype = DNA  length = 19
FEATURE                Location/Qualifiers
source                 1..19
                       mol_type = other DNA
                       note = Novel coronavirus 2019-nCoV forward primer (N)
                       organism = synthetic construct
SEQUENCE: 4
ctcactcaac atggcaagg                                               19

SEQ ID NO: 5           moltype = DNA  length = 26
FEATURE                Location/Qualifiers
source                 1..26
                       mol_type = other DNA
                       note = Novel coronavirus 2019-nCoV reverse primer (N)
                       organism = synthetic construct
SEQUENCE: 5
actgagatct ttcattttac cgtcac                                       26

SEQ ID NO: 6           moltype = DNA  length = 26
FEATURE                Location/Qualifiers
source                 1..26
                       mol_type = other DNA
                       note = Novel coronavirus 2019-nCoV probe (N)
                       organism = synthetic construct
SEQUENCE: 6
ctactaccga agagctacca gacgaa                                       26

SEQ ID NO: 7           moltype = DNA  length = 23
FEATURE                Location/Qualifiers
source                 1..23
                       mol_type = other DNA
                       note = Influenza A virus forward primer
                       organism = synthetic construct
SEQUENCE: 7
```

```
gtattactaa gggctttcac cga                                       23

SEQ ID NO: 8            moltype = DNA  length = 22
FEATURE                 Location/Qualifiers
source                  1..22
                        mol_type = other DNA
                        note = Influenza A virus reverse primer
                        organism = synthetic construct
SEQUENCE: 8
attccattca agtcctccga tg                                        22

SEQ ID NO: 9            moltype = DNA  length = 26
FEATURE                 Location/Qualifiers
source                  1..26
                        mol_type = other DNA
                        note = Influenza A virus probe
                        organism = synthetic construct
SEQUENCE: 9
aaaagaaggc aatggtgaga tttcgc                                    26

SEQ ID NO: 10           moltype = DNA  length = 21
FEATURE                 Location/Qualifiers
source                  1..21
                        mol_type = other DNA
                        note = Influenza B virus forward primer
                        organism = synthetic construct
SEQUENCE: 10
gagctgccta tgaagacctg a                                         21

SEQ ID NO: 11           moltype = DNA  length = 20
FEATURE                 Location/Qualifiers
source                  1..20
                        mol_type = other DNA
                        note = Influenza B virus reverse primer
                        organism = synthetic construct
SEQUENCE: 11
gctcccattc cttctacctg                                           20

SEQ ID NO: 12           moltype = DNA  length = 23
FEATURE                 Location/Qualifiers
source                  1..23
                        mol_type = other DNA
                        note = Influenza B virus probe
                        organism = synthetic construct
SEQUENCE: 12
tttgctggaa catggaaacc ctt                                       23

SEQ ID NO: 13           moltype = DNA  length = 22
FEATURE                 Location/Qualifiers
source                  1..22
                        mol_type = other DNA
                        note = Internal standard forward primer
                        organism = synthetic construct
SEQUENCE: 13
tttggtatcg tggaaggact ca                                        22

SEQ ID NO: 14           moltype = DNA  length = 19
FEATURE                 Location/Qualifiers
source                  1..19
                        mol_type = other DNA
                        note = Internal standard reverse primer
                        organism = synthetic construct
SEQUENCE: 14
gccatcacgc cacagtttc                                            19

SEQ ID NO: 15           moltype = DNA  length = 24
FEATURE                 Location/Qualifiers
source                  1..24
                        mol_type = other DNA
                        note = Internal standard probe
                        organism = synthetic construct
SEQUENCE: 15
accacagtcc atgccatcac tgcc                                      24

SEQ ID NO: 16           moltype = DNA  length = 24
FEATURE                 Location/Qualifiers
source                  1..24
                        mol_type = other DNA
                        note = Other novel coronavirus 2019-nCoV forward primer
```

```
                        (ORFlab)
                       organism = synthetic construct
SEQUENCE: 16
ccccaaaatg ctgttgttaa aatt                                           24

SEQ ID NO: 17          moltype = DNA  length = 25
FEATURE                Location/Qualifiers
source                 1..25
                       mol_type = other DNA
                       note = Other novel coronavirus 2019-nCoV reverse primer
                        (ORFlab)
                       organism = synthetic construct
SEQUENCE: 17
ttcaagccag attcattatg gtatt                                          25

SEQ ID NO: 18          moltype = DNA  length = 29
FEATURE                Location/Qualifiers
source                 1..29
                       mol_type = other DNA
                       note = Other novel coronavirus 2019-nCoV probe (ORFlab)
                       organism = synthetic construct
SEQUENCE: 18
tccagcatgt cacaattcag aagtaggac                                      29

SEQ ID NO: 19          moltype = DNA  length = 21
FEATURE                Location/Qualifiers
source                 1..21
                       mol_type = other DNA
                       note = Other novel coronavirus 2019-nCoV forward primer
                        (ORFlab)
                       organism = synthetic construct
SEQUENCE: 19
cccgcactct tgaaactgct c                                              21

SEQ ID NO: 20          moltype = DNA  length = 28
FEATURE                Location/Qualifiers
source                 1..28
                       mol_type = other DNA
                       note = Other novel coronavirus 2019-nCoV reverse primer
                        (ORFlab)
                       organism = synthetic construct
SEQUENCE: 20
tagattgtta gtagccaaat cagatgtg                                       28

SEQ ID NO: 21          moltype = DNA  length = 25
FEATURE                Location/Qualifiers
source                 1..25
                       mol_type = other DNA
                       note = Other novel coronavirus 2019-nCoV probe (ORFlab)
                       organism = synthetic construct
SEQUENCE: 21
ctgtgcgtgt tttacagaag gccgc                                          25

SEQ ID NO: 22          moltype = DNA  length = 25
FEATURE                Location/Qualifiers
source                 1..25
                       mol_type = other DNA
                       note = Other novel coronavirus 2019-nCoV forward primer
                        (ORFlab)
                       organism = synthetic construct
SEQUENCE: 22
gttgctcgaa atcaaagaca cagaa                                          25

SEQ ID NO: 23          moltype = DNA  length = 27
FEATURE                Location/Qualifiers
source                 1..27
                       mol_type = other DNA
                       note = Other novel coronavirus 2019-nCoV reverse primer
                        (ORFlab)
                       organism = synthetic construct
SEQUENCE: 23
cttgtaacct tgcacttcta tcacagt                                        27
```

-continued

```
SEQ ID NO: 24          moltype = DNA  length = 33
FEATURE                Location/Qualifiers
source                 1..33
                       mol_type = other DNA
                       note = Other novel coronavirus 2019-nCoV probe (ORFlab)
                       organism = synthetic construct
SEQUENCE: 24
ttgcacctaa tatgatggta acaaacaata cct                        33
```